United States Patent [19]

Peet et al.

[11] 4,419,357

[45] Dec. 6, 1983

[54] 3-(1H-TETRAZOL-5-YL)-4(3H)-QUINAZOLINONES

[75] Inventors: Norton P. Peet; Shyam Sunder, both of Indianapolis, Ind.

[73] Assignee: The Dow Chemical Company, Midland, Mich.

[21] Appl. No.: 340,577

[22] Filed: Jan. 18, 1982

[51] Int. Cl.³ .................. A61K 31/41; A61K 31/505; C07D 403/04
[52] U.S. Cl. ..................................... 424/251; 544/284
[58] Field of Search ........................ 544/284; 424/251

[56] References Cited

U.S. PATENT DOCUMENTS

| | | | |
|---|---|---|---|
| 3,265,969 | 8/1966 | Schipper | 544/284 |
| 4,035,368 | 7/1977 | Erickson | 424/258 |
| 4,122,274 | 10/1978 | Juby | 544/282 |
| 4,209,620 | 6/1980 | Juby | 544/252 |

FOREIGN PATENT DOCUMENTS 1523081 8/1978 United Kingdom .

OTHER PUBLICATIONS

Nohara et al., "Chemical Abstracts", vol. 84, 1976, Col. 84:59479a.
Erickson et al., "J. Med. Chem.", vol. 22, No. 7, 1979, pp. 816–825.

*Primary Examiner*—Mark L. Berch
*Assistant Examiner*—James H. Turnipseed
*Attorney, Agent, or Firm*—John J. Kolano; Gary D. Street; Richard G. Waterman

[57] ABSTRACT

3-(1H-tetrazol-5-yl)-4(3H)-quinazolinones useful as antiallergic agents are described herein. The compounds are prepared by the reaction of an appropriate 2-amino-N-(1H-tetrazol-5-yl)benzamide with an appropriate ortho ester.

11 Claims, No Drawings

3-(1H-TETRAZOL-5-YL)-4(3H)-QUINAZOLINONES

A variety of tetrazoles have been described in the literature and, particularly, compounds wherein the tetrazole is attached to another heterocyclic ring system through a carbon-carbon bond. The present invention, however, relates to compounds wherein the carbon atom of a tetrazole is attached to a nitrogen atom in another heterocyclic system. More particularly, the present invention relates to compounds having the following general formula:

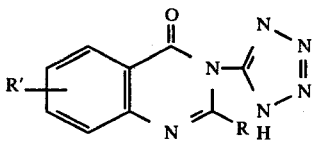

wherein R is hydrogen, $C_{1-4}$ lower alkyl or phenyl; R' is hydrogen, methyl, methoxy, halogen or the divalent group 6,7-methylenedioxy; and the pharmaceutically acceptable salts thereof.

Hydrogen is preferred for R but examples for the lower alkyl group referred to above for R are methyl, ethyl, propyl or butyl. Examples of halogen are fluorine, chlorine and bromine.

R' indicates monosubstitution at the 5-, 6-, 7- or 8-positions of the quinazolinone structure except when R' represents the divalent group methylenedioxy, in which case the substitution must be located at the 6,7-position.

Equivalent for the purposes of this invention are the pharmaceutically acceptable salts and also the hydrates of the compounds and their salts. The term "pharmaceutically acceptable salt" as used herein is intended to include non-toxic cationic salts such as the alkali metals salts, e.g., sodium and potassium; alkaline earth metal salts such as calcium, magnesium or barium; salts with ammonia; and salts with organic bases, e.g., amines such as triethyl amine, n-propyl amine and tri-n-butyl amine. The alkali metal salts and, particularly the sodium salt, are preferred.

The compounds of the present invention are prepared by the reaction of a 2-aminobenzamide of the formula:

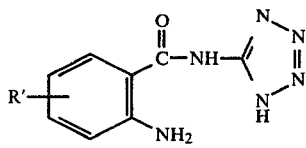

wherein R' is defined as above, with an ortho ester of the formula:

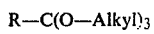

R—C(O—Alkyl)$_3$ wherein R is defined as above and Alkyl is preferably ethyl although it can contain 1-4 carbon atoms. The reactants are usually heated together at reflux in a slight excess of the ortho ester although it is also possible to make use of an appropriate inert solvent. Examples of useful solvents for the reaction are lower alkanols such as ethanol, or glycol monoethers such as 2-methoxyethanol or 1-methoxy-2-propanol.

In the final products, the tetrazole ring is reactive at the 1- and 2-positions and when the quinazolinone has no substituent at the 2-position, the tetrazole may be alkylated under the process conditions used here. Such a side reaction can be minimized in several ways, i.e., by avoiding an excess of the ortho ester, by avoiding prolonged heating or by distilling out the alcohol formed from reaction of the ortho ester.

The 2-aminobenzamide used as the starting material in the above process is obtained by catalytic hydrogenation of an alkaline solution of the corresponding 2-nitrobenzamide. The preferred catalyst is 5% Pd/C although similar catalysts, such as Pt/C, can also be used. The starting tetrazole is preferably dissolved in aqueous 1N sodium hydroxide solution and, if necessary, this can be diluted with ethanol or additional water.

The necessary 2-nitrobenzamide is obtained by the reaction of the appropriate 2-nitrobenzoyl chloride with 5-aminotetrazole and the necessary acid chloride is obtained from the corresponding carboxylic acid, all using standard procedures.

The compounds obtained above are converted to the pharmaceutically acceptable salts by reacting the tetrazole final product with a substantially equimolar amount of the appropriate base in an aqueous solution or in a suitable organic solvent such as methanol or ethanol. The salts are recovered by standard methods such as filtration if they are insoluble in the original medium, or, if they are soluble in that medium, the salt is precipitated by evaporation of the solvent or by addition of a non-solvent for the salt.

The compounds of the present invention are stable as solids and degrade very slowly in neutral solution although the degradation can be more rapid in alkaline or acid solutions.

The compounds of the present invention possess antiallergic activity. Thus, they are useful in the treatment of conditions in which antigen-antibody reactions are responsible for disease and particularly in the treatment of allergic diseases such as (but not limited to) extrinsic asthma, hay fever, urticaria, eczema or atopic dermatitis and upper respiratory conditions such as allergic rhinitis.

The compounds of the present invention may be administered either as individual therapeutic agents or as mixtures with other therapeutic agents. They may be administered alone but are generally administered in the form of pharmaceutical compositions, i.e., mixtures of the active agents with suitable pharmaceutical carriers or diluents. Examples of such compositions include tablets, lozenges, capsules, powders, aerosol sprays, aqueous or oily suspensions, syrups, elixirs and aqueous solutions for injection. The compounds are most preferably administered in oral dosage forms.

The nature of the pharmaceutical composition and the pharmaceutical carrier or diluent will, or course, depend on the desired route of administration, i.e., orally, parenterally or by inhalation. Oral compositions may be in the form of tablets or capsules and may contain conventional excipients such as binding agents (e.g., syrup, acacia, gelatin, sorbitol, tragacanth or polyvinylpyrrolidone), fillers (e.g., lactose, sugar, maizestarch, calcium phosphate, sorbitol or glycine), lubricants (e.g., magnesium stearate, talc, polyethylene glycol, or silica), disintegrants (e.g., starch) or wetting agents (e.g., sodium lauryl sulfate). Oral liquid preparations may be in the form of aqueous or oily suspensions, solutions, emulsions, syrups, elixirs, etc., or may be presented as a dry product for reconstitution with water or other suitable vehicle before use. Such liquid preparations may contain conventional additives such as suspending agents, flavoring agents, diluents or emulsifying agents. For parenteral administration of inhalation, solutions or suspensions of a compound of formula 1 with conventional pharmaceutical vehicles may be employed, e.g., as an aerosol spray for inhalation, as an aqueous solution for intravenous injection or as an oily suspension for intramuscular injection. The compounds may also be administered by means of inhalers or other devices which permit the active compounds in the form of dry powders to come into direct contact with the lungs.

The compounds of the present invention or pharmaceutical compositions thereof may be administered to human asthmatic patients in single oral doses of approximately 1-1000 mg of active ingredient and multiple oral doses totalling up to about 4000 mg/day of active ingredient. When administered by inhalation, lower doses are generally given, i.e., on the order of about 0.1 of the normal dosage for the particular compound in question. These values are illustrative only, however, and the physician of course will ultimately determine the dosage most suitable for a particular patient on the basis of factors such as age, weight, diagnosis, severity of the symptoms and the particular agent to be administered.

The antiallergic activity of the present compounds is demonstrated by the IgE mediated rat Passive Cutaneous Anaphylaxis (PCA) test. This test is generally accepted as one of the best animal models for the qualitative determination of antiallergic activity. Disodium cromoglycate is active in this test when administered i.p. but not orally. The method can be described briefly as follows:

PCA Test Method

1. Antisera—Various standard methods described in the literature were used for the preparation of reaginic antisera to ovalbumin in either Hooded Lister or Brown Norway adult rats.
2. Animals—Adult male Sprague-Dawley or female Wistar Kyoto rats were used as antisera recipients in the test. The animals were allowed to acclimate for 5-14 days with food and water ad lib.
3. Sensitization—Recipient rats were passively sensitized by the intradermal injection of 100 microliters of two dilutions of antiserum (one injection on each side of the back). Sensitization occurred 48-72 hours prior to antigen challenge.
4. Administration of Test Compound—Four to six animals were used for each test compound/dilution. Compounds were homogenized in an appropriate carrier solution, and administered i.p. at 60 mg/kg 5 minutes prior to challenge or p.o. at 100 mg/kg 5 to 240 minutes prior to challenge.
5. Antigen Challenge and Reaction Evaluation—Ovalbumin (0.1-1.0 mg in a 0.5% solution of Evan's Blue dye) in saline was given to each rat by i.v. administration. Thirty minutes later, the resultant PCA reactions were measured for average diameter and color intensity from the reflected surface of the skin. Test compound activity is expressed as percent inhibition based on control reactions.

When tested by the above procedure, the compounds of the present invention were active both i.p. and orally.

As indicated earlier, those compounds wherein R is hydrogen are preferred. In addition to activity in the PCA test as described above, the compounds wherein R is hydrogen also inhibit the release of histamine in the rat Passive Peritoneal Anaphylaxis (PPA) test. This method can be described briefly as follows:

PPA TEST METHOD

1. Antisera—Reaginic antibody to ovalbumin for this test was prepared in adult male $B_6D_2F_1$ mice.
2. Animals—Adult male Sprague Dawley or female Wistar Kyoto rats were used as antibody recipients. The animals were allowed to acclimate for 5-14 days with food and water ad lib.
3. Sensitization—Recipient rats were sensitized i.p. with 2 ml of an appropriate saline dilution of the mouse anti-ovalbumin antiserum determined from prior experiments. Sensitization took place 2 hours prior to antigen challenge.
4. Administration of Test Compound—Five to ten animals were used for each test compound/dilution. Compounds were homogenized in saline with an equivalent of sodium bicarbonate to effect solubilization, if appropriate, and administered i.p. at 60 $\mu$g, 30 seconds prior to antigen challenge or p.o. 5 to 60 minutes prior to antigen challenge.
5. Antigen Challenge and Assay Evaluation—Two mg of ovalbumin in 5 ml of modified Tyrode's Solution was administered by i.p. injection and the animals were sacrificed 5 minutes later. Peritoneal shock fluids were collected and classified by centrifugation. Protein was removed from the samples by perchloric acid precipitation and subsequent centrifugation. The samples were then analyzed for histamine content by an automated fluorometric assay. Histamine levels of peritoneal shock fluids from treatment animals were then compared to those of shock fluids from control animals. Drug effect was expressed as percent inhibition of histamine release.

The following examples are presented to illustrate the present invention but they should not be construed as limiting it in any way.

EXAMPLE 1

To a slurry of 78 g of 4,5-methylenedioxy-2-nitrobenzaldehyde and 1.5 liter of water there was added a solution of 90 g of potassium permanganate in 1.5 liter of water over a period of 45 minutes. The mixture was then stirred at 70°-80° C. for an additional hour and then made alkaline with 400 ml of aqueous 10% potassium hydroxide. The mixture was filtered while hot to remove the precipitate which was washed with 2 portions of hot water. The filtrate was cooled for 16 hours and the solid which formed was separated by filtration to give recovered starting material. The new filtrate was acidified with concentrated hydrochloric acid and allowed to stand for 3 hours. The yellow solid which formed was separated by filtration to give crude product. The filtrate obtained was extracted with 4 portions of ethyl acetate and the combined extracts were dried over sodium sulfate and added to a solution of the previously obtained crude product in ethyl acetate. The ethyl acetate solution was concentrated, the resulting solid was slurried with chloroform, separated by filtration and dried to give 4,5-methylenedioxy-2-nitrobenzoic acid melting at about 160°-163° C.

EXAMPLE 2

A mixture of 25 g of 2-methyl-6-nitrobenzoic acid and 28.7 g of phosphorus pentachloride in 300 ml of cyclohexane was heated at reflux for 1 hour. The solution was concentrated and the residue was twice treated with chloroform and concentrated again to remove readily volatile materials and leave, as a residue, 2-methyl-6-nitrobenzoyl chloride as an oil.

To a warm solution of 28 g of 5-aminotetrazole monohydrate in 300 ml of tetrahydrofuran and 15 ml of water was added 26.7 g of 2-methyl-6-nitrobenzoyl chloride in 50 ml of tetrahydrofuran. The solution was allowed to stand for 16 hours, the solvent was evaporated and the residue was treated with water. The solid obtained was separated by filtration, slurried with ether and again separated by filtration to give 2-methyl-6-nitro-N-(1H-tetrazol-5-yl)benzamide melting at about 230°–232° C.

EXAMPLE 3

Using the appropriate reactants, the procedure as described in Example 2 was repeated to give the corresponding products as follows The reaction of 36.2 g of 5-methyl-2-nitrobenzoic acid and 41.6 g of phosphorus pentachloride in 150 ml of toluene gave a crude product which was treated with methylene chloride to give 5-methyl-2-nitrobenzoyl chloride as an oil. When 30 g of this acid chloride in 50 ml of tetrahydrofuran was added to a warm solution of 30.9 g of 5-aminotetrazole monohydrate in 600 ml of tetrahydrofuran and 30 ml of water, a precipitate formed quickly. This was allowed to stand for 1 hour, the white solid was separated by filtration, washed with water and air dried to give 5-methyl-2-nitro-N-(1H-tetrazol-5-yl)benzamide melting at about 278°–279° C.

The reaction of 50 g of 3-methyl-2-nitrobenzoic acid and 57.5 g of phosphorus pentachloride in 300 ml of cyclohexane gave, after treatment of the crude product with methylene chloride, 3-methyl-2-nitrobenzoyl chloride melting at about 81°–82° C. A solution of 53.1 g of this acid chloride and 50 ml of tetrahydrofuran was added to a warm solution of 55 g of 5-aminotetrazole monohydrate in 500 ml of tetrahydrofuran and 20 ml of water. The reaction was exothermic, a white precipitate formed and the mixture was allowed to stand for 4 hours. It was then diluted with water, the white precipitate was separated by filtration, washed with water and air dried to give 3-methyl-2-nitro-N-(1H-tetrazol-5-yl)benzamide melting at about 262°–263° C., with decomposition, after recrystallization from a mixture of dimethylformamide and water.

Reaction of 100 g of 5-chloro-2-nitrobenzoic acid and 103.3 g of phosphorus pentachloride in 400 ml of cyclohexane at reflux for 80 minutes followed by treatment of the crude product 3 times with carbon tetrachloride gave 5-chloro-2-nitrobenzoyl chloride. A solution of the acid chloride in 50 ml of tetrahydrofuran was added to a warm solution of 91.3 g of 5-aminotetrazole monohydrate in 500 ml of tetrahydrofuran and 20 ml of water. A precipitate formed, and the mixture was allowed to stand for 4 hours. It was then diluted with water and the solid was separated by filtration and air dried to give 5-chloro-2-nitro-N-(1H-tetrazol-5-yl)benzamide melting at about 268°–269° C., after recrystallization from dimethylformamide.

Reaction of 30 g of 3-methoxy-2-nitrobenzoic acid and 31.6 g of phosphorus pentachloride in 400 ml of methylene chloride at reflux for 2 hours followed by treatment of the crude product obtained with toluene 3 times gave 3-methoxy-2-nitrobenzoyl chloride as a solid. A solution of 30 g of this acid chloride in 50 ml of tetrahydrofuran was added to a solution of 28.7 g of 5-aminotetrazole monohydrate in 300 ml of tetrahydrofuran and 15 ml of water. A white precipitate appeared immediately but the mixture was allowed to stand for 3 hours. It was then diluted with water and the white solid was separated by filtration and air dried to give 3-methoxy-2-nitro-N-(1H-tetrazol-5-yl)benzamide melting at about 271° C. after recrystallization from dimethylformamide.

Reaction of 31.7 g of 4,5-methylenedioxy-2-nitrobenzoic acid and 31.2 g of phosphorus pentachloride in 250 ml of cylohexane at reflux for 30 minutes followed by treatment of the crude oil twice with carbon tetrachloride gave 4,5-methylenedioxy-2-nitrobenzoyl chloride. The acid chloride was dissolved in 50 ml of tetrahydrofuran and added to a warm solution of 30.9 g of 5-aminotetrazole monohydrate in 750 ml of tetrahydrofuran and 30 ml of water. The solution was stirred for 30 minutes and then diluted with 3 liters of water. The solid which formed was separated by filtration and dried to give 4,5-methylenedioxy-2-nitro-N-(1H-tetrazol-5-yl)benzamide melting at about 279° C. after recrystallization from a mixture of dimethylformamide and water.

To a solution of 10.3 g of 5-aminotetrazole monohydrate in 300 ml of tetrahydrofuran and 15 ml of water was added 9.3 g of 2-nitrobenzoyl chloride. The solution was allowed to stand for 30 minutes before it was diluted with 200 ml of water and stored in a refrigerator for 72 hours. The solid which formed was separated by filtration to give 2-nitro-N-(1H-tetrazol-5-yl)benzamide melting at about 272°–273° C. with decomposition.

EXAMPLE 4

A solution was prepared from 7.5 g of 2-methyl-6-nitro-N-(1H-tetrazol-5-yl)benzamide in 100 ml of aqueous 1N sodium hydroxide. A 0.5-g quantity of 5% Pd/C was added and the mixture was hydrogenated in a Parr apparatus at 3.3 atmospheres until uptake of hydrogen stopped (75 minutes). The catalyst was removed by filtration and the filtrate was treated with 100 ml of aqueous 1N hydrochloric acid. The white solid which formed was separated by filtration and air dried to give 2-amino-6-methyl-N-(1H-tetrazol-5-yl)benzamide melting at about 248° C. with decomposition.

EXAMPLE 5

Using the appropriate reactants, the procedure as described in Example 4 was repeated to give the appropriate corresponding products as follows Hydrogenation of 24.8 g of 5-methyl-2-nitro-N-(1H-tetrazol-5-yl)benzamide in 125 ml of aqueous 1N sodium hydroxide and 100 ml of ethanol gave 2-amino-5-methyl-N-(1H-tetrazol-5-yl)benzamide melting at about 245°–246° C. after recrystallization from ethanol.

Hydrogenation of 3-methyl-2-nitro-N-(1H-tetrazol-5-yl)benzamide gave 2-amino-3-methyl-N-(1H-tetrazol-5-yl)benzamide melting at about 258°–259° C. (dec) after recrystallization from a mixture of dimethylformamide and methanol.

Hydrogenation of 5-chloro-2-nitro-N-(1H-tetrazol-5-yl)benzamide using 0.5 g of 5% Pt/C catalyst gave 2-amino-5-chloro-N-(1H-tetrazol-5-yl)benzamide melting at about 255° C. after recrystallization from dimethylformamide.

Hydrogenation of 3-methoxy-2-nitro-N-(1H-tetrazol-5-yl)benzamide gave 2-amino-3-methoxy-N-(1H-tetrazol-5-yl)benzamide melting at about 268°-269° C. after recrystallization from a mixture of dimethylformamide and water.

Hydrogenation of 10 g of 4,5-methylenedioxy-2-nitro-N-(1H-tetrazol-5-yl)benzamide in 40 ml of aqueous 1N sodium hydroxide solution and 160 ml of water and using 1 g of 10% Pd/C gave 2-amino-4,5-methylenedioxy-N-(1H-tetrazol-5-yl)benzamide as brown needles melting at about 255° C. (dec) after recrystallization from a mixture of dimethylformamide and water.

Hydrogenation of 19 g of 2-nitro-N-(1H-tetrazol-5-yl)benzamide in 100 ml of aqueous 1N sodium hydroxide solution and 100 ml of ethanol using 0.5 g of 5% Pd/C catalyst and 2 atmospheres pressure gave 2-amino-N-(1H-tetrazol-5-yl)benzamide melting at about 253°-254° C.

EXAMPLE 6

A mixture of 1.3 g of 2-amino-6-methyl-N-(1H-tetrazol-5-yl)benzamide and 10 ml of triethoxymethane was heated at reflux for 1 hour. The mixture was then cooled and the solid which formed was separated by filtration, washed with ethanol and air dried to give 5-methyl-3-(1H-tetrazol-5-yl)-4(3H)-quinazolinone melting at about 280°-281° C. with decomposition. This compound has the following structural formula:

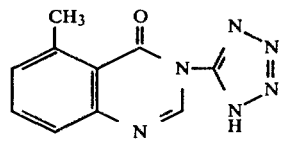

EXAMPLE 7

Using the appropriate reactants, the procedure as described in Example 6 was repeated to give the appropriate corresponding products as follows 2-Amino-5-methyl-N-(1H-tetrazol-5-yl)benzamide in an excess of triethoxymethane was refluxed for 60 hours to give 6-methyl-3-(1H-tetrazol-5-yl)-4(3H)-quinazolinone melting at about 285°-286° C. after recrystallization from a mixture of dimethylsulfoxide and water.

Reaction of 2-amino-3-methyl-N-(1H-tetrazol-5-yl)benzamide with triethoxymethane gave 8-methyl-3-(1H-tetrazol-5-yl)-4(3H)-quinazolinone melting at about 268° C. (dec) after recrystallization from dimethylformamide.

A suspension of 2.73 g of 2-amino-5-chloro-N-(1H-tetrazol-5-yl)benzamide in 9 ml of triethoxymethane was refluxed for 4.5 hours to give 6-chloro-3-(1H-tetrazol-5-yl)-4(3H)-quinazolinone melting at about 241° C. (dec).

A suspension of 5.3 g of 2-amino-3-methoxy-N-(1H-tetrazol-5-yl)benzamide in 30 ml of triethoxymethane was refluxed for 14 hours to give 8-methoxy-3-(1H-tetrazol-5-yl)-4(3H)-quinazolinone melting at about 260°-261° C. (dec) after recrystallization from dimethylformamide.

EXAMPLE 8

A slurry of 11.6 g of 2-amino-4,5-methylenedioxy-N-(1H-tetrazol-5-yl)benzamide and 25 g of triethoxymethane in 150 ml of 2-methoxyethanol was heated at reflux for 1 hour. A complete solution was not obtained at any time but the final mixture was filtered and the separated solid was air dried and recrystallized from a mixture of dimethylformamide and methanol to give 6,7-methylenedioxy-3-(1H-tetrazol-5-yl)-4(3H)-quinazolinone melting at about 280° C. (dec).

EXAMPLE 9

A mixture of 326 g of 2-amino-N-(1H-tetrazol-5-yl)benzamide, 680 ml of triethoxymethane and 2 liters of 1-methoxy-2-propanol was heated at reflux. The ethanol which formed was removed through a reflux head. After about 30-60 minutes with a pot temperature above 100° C., HPLC showed that all the starting material had reacted. The mixture was then cooled to 10° C. and the solid which formed was separated by filtration, washed with methanol and dried. The crude product was dissolved in hot dimethylformamide and the solution was diluted with methanol and cooled. The solid which precipitated was separated by filtration to give 3-(1H-tetrazol-5-yl)-4(3H)-quinazolinone melting at about 259°-260° C. This compound has the following structural formula:

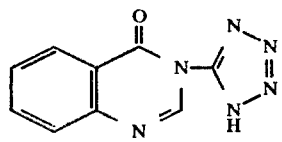

EXAMPLE 10

A mixture of 3.8 g of 2-amino-N-(1H-tetrazol-5-yl)benzamide and 3.3 g of 1,1,1-triethoxyethane in 50 ml of ethanol was heated at reflux for 18 hours. The mixture was then concentrated to a small volume and the resulting solid was collected by filtration and air dried to give 2-methyl-3-(1H-tetrazol-5-yl)-4(3H)-quinazolinone melting at about 225°-226° C. This compound has the following structural formula:

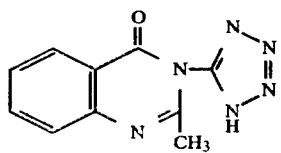

EXAMPLE 11

When the procedure of Example 10 was repeated using 1,1,1-triethoxypropane or (triethoxymethyl)benzene in place of the 1,1,1-triethoxyethane, the products obtained are, respectively, 2-ethyl-3-(1H-tetrazol-5-yl)-4(3H)-quinazolinone melting at about 210°-212° C. and 2-phenyl-3-(1H-tetrazol-5-yl)-4(3H)-quinazolinone melting at about 252°-253° C. after recrystallization from ethanol.

A slurry of 7.0 g of 2-amino-5-methyl-N-(1H-tetrazol-5-yl)benzamide and 5.7 g of 1,1,1-triethoxypropane in 50 ml of 2-methoxyethanol was heated at reflux for 48 hours. The solution was cooled and concentrated to a small volume. The resulting solid was then collected and air dried to give 2-ethyl-6-methyl-3-(1H)-tetrazol-5-yl)-4(3H)-quinazolinone melting at about 204°-205° C., after recrystallization from a mixture of dimethylformamide and water.

EXAMPLE 12

A mixture of 1 g of 6,7-methylenedioxy-3-(1H-tetrazol-5-yl)-4(3H)-quinazolinone in 4 ml of aqueous 1N sodium hydroxide and 30 ml of water was heated to 40° C. The resulting solution was diluted with 150 ml of 2-propanol and filtered to remove a small amount of insoluble material and the filtrate was cooled in an ice bath. The precipitate which formed was separated by filtration and air dried to give the sodium salt of 6,7-methylenedioxy-3-(1H-tetrazol-5-yl)-4(3H)-quinazolinone (monohydrate) which did not melt when heated up to 300° C.

EXAMPLE 13

A slurry of 10.7 g of 2-methyl-3-(1H-tetrazol-5-yl)-4(3H)-quinazolinone in 20 ml of water was prepared and then aqueous 5N sodium hydroxide solution was added until complete solution took place at 65°–70° C. Then 75 ml of absolute ethanol was added and the mixture was cooled in in ice bath. The white which formed was separated by filtration and recrystallized from a mixture of 15 ml of water and 60 ml of ethanol to give the sodium salt of 3-(1H-tetrazol-5-yl)-4(3H)-quinazolinone (monohydrate). This compound has the following structural formula:

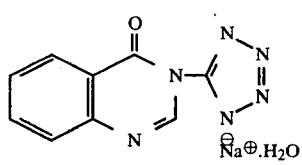

What is claimed is:
1. A compound of the formula:

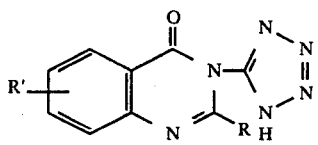

wherein R is hydrogen, $C_{1-4}$ lower alkyl or phenyl; R' is hydrogen, methyl, methoxy, halogen or the divalent group 6,7-methylenedioxy; and the pharmaceutically acceptable salts thereof.

2. A compound according to claim 1 which has the formula:

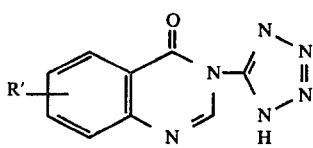

wherein R' is hydrogen, methyl, methoxy, halogen or the divalent group 6,7-methylenedioxy; and the alkali metal salts thereof.

3. A compound according to claim 1 which is 3-(1H-tetrazol-5-yl)-4(3H)-quinazolinone.

4. A compound according to claim 1 which is the sodium salt of 3-(1H-tetrazol-5-yl)-4(3H)-quinazolinone.

5. A compound according to claim 1 which has the formula:

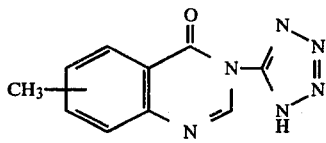

and the alkali metal salts thereof.

6. A compound according to claim 1 which is 6-methyl-3-(1H-tetrazol-5-yl)-4(3H)-quinazolinone.

7. A compound according to claim 1 which is 6,7-methylenedioxy-3-(1H-tetrazol-5-yl)-4(3H)-quinazolinone.

8. A method for inhibiting the result of antibody-antigen reactions in mammals which comprises administration to a mammal susceptible to allergic reaction of an effective amount of a compound of the formula:

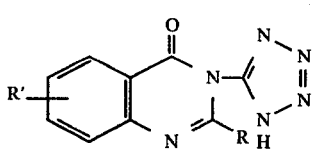

wherein R is hydrogen, $C_{1-4}$ lower alkyl or phenyl; R' is hydrogen, methyl, methoxy, halogen or the divalent group 6,7-methylenedioxy; and the pharmaceutically acceptable salts thereof.

9. A method according to claim 8 which comprises administration of an effective amount of a compound of the formula:

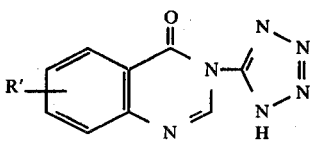

wherein R' is hydrogen, methyl, methoxy, halogen or the divalent group 6,7-methylenedioxy; and the alkali metal salts thereof.

10. A method according to claim 8 which comprises administration of an effective amount of 3-(1H-tetrazol-5-yl)-4(3H)-quinazolinone.

11. A method according to claim 8 which comprises administration of an effective amount of the sodium salt of 3-(1H-tetrazol-5-yl)-4(3H)-quinazolinone.

* * * * *

UNITED STATES PATENT AND TRADEMARK OFFICE
CERTIFICATE OF CORRECTION

PATENT NO. : 4,419,357
DATED : December 6, 1983
INVENTOR(S) : Norton P. Peet and Shyam Sunder It is certified that error appears in the above–identified patent and that said Letters Patent are hereby corrected as shown below:

Column 3, line 5, "administration of" should read -- administration or --.

Column 9, line 23, "in in ice bath." should read -- in an ice bath. --.

Column 9, line 23, after "The white" insert the word -- solid --.

Signed and Sealed this

Tenth Day of April 1984

[SEAL]

Attest:

GERALD J. MOSSINGHOFF

Attesting Officer     Commissioner of Patents and Trademarks